(12) United States Patent
Stéphan et al.

(10) Patent No.: US 11,472,767 B2
(45) Date of Patent: Oct. 18, 2022

(54) PROCESS FOR THE MONOTOPIC PREPARATION OF INTERMEDIATE ORGANO-IODINATED COMPOUNDS FOR THE SYNTHESIS OF IOVERSOL

(71) Applicant: GUERBET, Villepinte (FR)

(72) Inventors: Pellinghelli Stéphan, Bruyeres sur Oise (FR); Myriam Petta, Montmorency (FR)

(73) Assignee: GUERBET, Villepinte (FR)

( * ) Notice: Subject to any disclaimer, the term of this patent is extended or adjusted under 35 U.S.C. 154(b) by 0 days.

(21) Appl. No.: 17/265,107

(22) PCT Filed: Aug. 2, 2019

(86) PCT No.: PCT/EP2019/070869
§ 371 (c)(1),
(2) Date: Feb. 1, 2021

(87) PCT Pub. No.: WO2020/025787
PCT Pub. Date: Feb. 6, 2020

(65) Prior Publication Data
US 2021/0284597 A1 Sep. 16, 2021

(30) Foreign Application Priority Data
Aug. 2, 2018 (FR) ...................... 18 57242

(51) Int. Cl.
C07C 231/02 (2006.01)

(52) U.S. Cl.
CPC ................... *C07C 231/02* (2013.01)

(58) Field of Classification Search
None
See application file for complete search history.

(56) References Cited

U.S. PATENT DOCUMENTS

| | | | |
|---|---|---|---|
| 3,210,412 A | 10/1965 | Chapman | |
| 4,141,894 A | 2/1979 | Zimmerman | |
| 5,670,136 A | 9/1997 | Bacon et al. | |
| 10,836,711 B2 * | 11/2020 | Petta | C07D 319/06 |
| 2020/0002269 A1 | 1/2020 | Petta et al. | |

FOREIGN PATENT DOCUMENTS

| | | | |
|---|---|---|---|
| CN | 106496058 | * | 3/2017 |
| CN | 107698456 | * | 2/2018 |
| GB | 2496971 A | | 5/2013 |
| IN | 187816 | * | 10/1998 |
| WO | 9616927 A1 | | 6/1996 |
| WO | 9637460 A1 | | 11/1996 |
| WO | 06100731 A1 | | 9/2006 |
| WO | 2012175903 A1 | | 12/2012 |
| WO | WO2016193740 | * | 12/2016 |

OTHER PUBLICATIONS

Bjorsvik ("N-Acylation Reactions Performed in Aqueous Reaction Medium: Screening and Optimising of a Synthetic Step of a Process for Iodixanol" Organic Process Research and Development, 6(2), 2002, p. 113-119) (Year: 2002).*
"Constitute", v. Oxford English Dictionary Online, 2020, 4 pages, Oxford University Press, retrieved from <https://www.bed.com/view/Entry/39844?print> on Feb. 6, 2020.
Fontanive et al., "Myelography Iodinated Contract Media. I Unraveling the Atropisomerism Properties in Solution", Molecular Pharmaceutics, 2015, pp. 1939-1950, vol. 12.
Hayashi, "Pot Economy and One-Pot Synthesis", Chemical Science, 2016, pp. 866-880, vol. 7.
Smith et al., "March's Advanced Organic Chemistry: Reactions, Mechanisms, and Structure, Sixth Edition", 2007, p. 425, John Wiley & Sons, Inc.

* cited by examiner

*Primary Examiner* — Amy C Bonaparte
(74) *Attorney, Agent, or Firm* — Thompson Coburn LLP; Steven M. Ritchey

(57) ABSTRACT

A process for preparing an organo-iodinated compound, comprising the following steps:
a) acylating 2,4,6-triiodo-5-aminoisophthalic acid of formula (A) below:

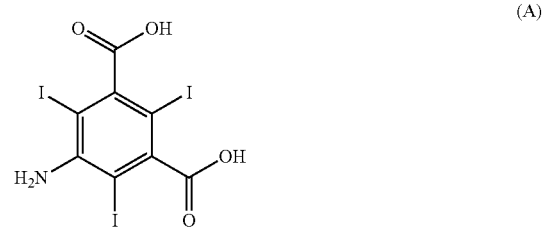

(A)

to obtain an intermediate compound Ya;
b) chlorinating the intermediate compound Ya to obtain an organo-iodinated intermediate compound Yb;
c) amidating the organo-iodinated intermediate compound Yb to obtain an intermediate compound Yc; and
d) deprotecting the intermediate compound Yc, the steps a), b), c) and d) being carried out without isolation of at least one intermediate compound chosen from Ya and Yc.

16 Claims, No Drawings

PROCESS FOR THE MONOTOPIC PREPARATION OF INTERMEDIATE ORGANO-IODINATED COMPOUNDS FOR THE SYNTHESIS OF IOVERSOL

CROSS-REFERENCE TO RELATED APPLICATIONS

This application is a U.S. National Phase application of PCT/EP2019/070869 filed on Aug. 2, 2019, claiming the benefit of French Application No. 18 57242, filed on Aug. 2, 2018, both of which are incorporated herein by reference in their entireties.

The present invention relates to a process for preparing organo-iodinated compounds, and also the preparation intermediates thereof. More particularly, the present invention relates to a process for preparing organo-iodinated compounds of use as preparation intermediates in the synthesis of the iodinated contrast agent ioversol (Optiray®).

Ioversol is described as a nonionic contrast agent in U.S. Pat. No. 4,396,598.

Currently, the majority of processes for the synthesis of iodinated contrast agents, and notably the process concerning ioversol, use, as intermediate product, 5-amino-2,4,6-triiodoisophthalic acid dichloride (also known as DiCOCl), having the following formula:

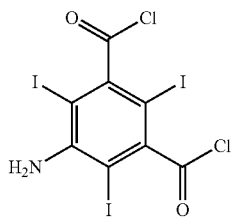 [SMILES: Nc1c(I)c(C(=O)Cl)c(I)c(C(=O)Cl)c1I]

During the synthesis of iodinated contrast agents, it is necessary to carry out lengthy separation and purification steps in order to obtain synthesis intermediates with a good degree of purity. These steps considerably increase the time for carrying out the synthesis, and thus increase the costs involved in employing those methods for the preparation of contrast agents.

One of the steps in the production of DiCOCl is a step of chlorination (also known as chloride formation) of 5-amino-2,4,6-triiodoisophthalic acid (AATI) with a chlorinating agent such as thionyl chloride, also known as thionyl dichloride ($SOCl_2$). This chlorination is a slow step (reaction time of more than 7 hours 30 minutes) and is energy-consuming because it is carried out at a high temperature of more than 48° C. A large excess of chlorinating agent with respect to the AATI means that the kinetics are faster, but using such an excess is not acceptable from an industrial and environmental viewpoint. In fact, in contact with water, thionyl chloride releases hydrogen chloride (HCl) and sulfur dioxide ($SO_2$), which are corrosive and irritant gases. The use of catalysts for this chlorination reaction has been recommended in order to be able to reduce the quantity of $SOCl_2$ used while obtaining a good industrial yield.

The processes used for preparing DiCOCl also suffer from the disadvantage of generating a large quantity of effluents because large quantities of water are used at the time of the "precipitating" hydrolysis of the DiCOCl obtained from the chlorination step. As an example, in the application EP 0 794 937, the addition of 22.2 to 33 equivalents of water per equivalent of AATI is described (Examples 1 to 3), or in application EP 0 773 925, the addition of 120 equivalents of water is described for the hydrolysis of thionyl chloride (see Example 1-E). Finally, these processes necessitate carrying out purification steps by precipitation, filtration and drying, in order to ensure that the reactivity is optimal and the yield is competitive in the subsequent steps. It should also be noted that the drying step may prove to be dangerous because it runs an industrial risk of exothermic degradation, and thus has to be carried out under highly controlled and restrictive conditions.

Following this chlorination step, the DiCOCl is acylated. This step is very lengthy because it can last several tens of hours (sometimes up to 70 hours). It also involves steps of purification and isolation by draining and drying in order to obtain a synthesis intermediate of iodinated contrast agents. The drying step presents the risk highlighted above. In addition, this step involves the use of large excesses of certain reagents which may, in some cases, prove to be expensive, whether this is in terms of their purchase or even their synthesis. Handling of certain of these reagents (for example DiCOCl) may also pose problems because of their particle size. For this acylation step alone, yields are obtained which are limited to approximately 87.5%. The yield for the chlorination step is approximately 90.5%. The yield for the combination of the chlorination and acylation steps is thus approximately 79.2%.

Preparation processes involving an acylation followed by a chlorination which also suffer from the same disadvantages as those mentioned above are also known.

In particular, the application WO 2012/175903 describes obtaining an acylated AATI obtained using a large excess of acylating agent. This acylated intermediate compound is then isolated, filtered and dried before being chlorinated.

As a consequence, there is a need for an improved process for preparing iodinated contrast agents. More particularly, there is a need for a process for preparing iodinated contrast agents that can be applied on an industrial scale, and which is more economical, rapid and safe.

Several patents describe processes for preparing ioversol or some of the synthesis intermediates thereof: U.S. Pat. No. 4,997,983, EP 0 484 328 (AATI preparation process), EP 0 598 751 (process for preparing an ioversol synthesis intermediate from a compound other than AATI, without using acetoxyacetyl chloride (also known as 2-chloro-2-oxoethyl acetate or AAC) and by using DMAC and chloroacetyl chloride (also known as CAC), EP 0 640 067 (process for preparing ioversol from a compound other than AATI). Others describe processes for purifying these compounds: EP 0 618 836, EP 0 646 021, EP 0 863 782, EP 1 551 522, EP 0 700 377, EP 0 470 247, EP 0 907 395, EP 0 515 480.

Other patents describe certain parts of this synthesis: EP 2 281 807 and EP 2 277 846.

The aim of the present invention is to provide a process for preparing organo-iodinated products, and more particularly synthesis intermediates of the iodinated contrast agent ioversol, enabling the abovementioned disadvantages to be overcome.

The aim of the present invention is also to provide a process for preparing organo-iodinated compounds which can be applied on an industrial scale, in particular a safe, rapid and economical process which is acceptable from an environmental viewpoint.

The aim of the present invention is to provide a process for preparing organo-iodinated compounds that are synthesis intermediates of the iodinated contrast agent ioversol which have a good yield, and in particular a better yield compared with known processes.

Thus, the present invention relates to a process for preparing an organo-iodinated compound, comprising the following steps:
a) acylation of 2,4,6-triiodo-5-aminoisophthalic acid of formula (A) below:

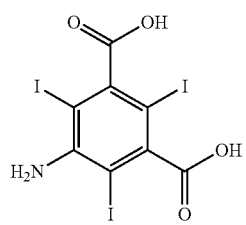

(A)

in order to obtain an intermediate compound Ya; then
b) chlorination of the intermediate compound Ya in order to obtain an organo-iodinated intermediate compound Yb; then
c) amidation of the organo-iodinated intermediate compound Yb in order to obtain an intermediate compound Yc; then
d) deprotection of the intermediate compound Yc, the steps a), b), c) and d) being carried out without isolation of at least one intermediate compound chosen from Ya and Yc.

Surprisingly, the inventors have implemented a one-pot process that makes it possible to carry out the steps a) of acylation, b) of chlorination, c) of amidation and d) of deprotection without the need to isolate at least one of the intermediate compounds Ya and Yc, notably without isolation of the intermediate compounds Ya and Yc. Thus, acylation of the AATI is carried out, then is directly followed by chlorination of said acylated AATI without isolation of the intermediate compound Ya, which is itself followed by an amidation of the compound Yb, preferably without purification of the intermediate compound Yb, and by the deprotection of the compound Yc without isolation of the intermediate compound Yc.

The succession of steps a) of acylation, b) of chlorination, c) of amidation and d) of deprotection as according to the invention is preferably performed in one and the same reaction medium, and therefore corresponds to a one-pot sequence.

The preparation process according to the invention advantageously makes it possible to avoid the steps of separation and purification of the intermediate compounds such as the synthesis intermediate compounds Ya and/or Yc: the use of precipitation or washing solvents is reduced or avoided, and also the treatment of the corresponding mother liquors. The preparation process according to the invention is thus cheaper, faster and more environmentally friendly.

Generally, the process is free of addition of a nonsolvent of the intermediate compound Ya during step a) and between steps a) and b). A "nonsolvent of the intermediate compound" is understood to mean a solvent in which the intermediate compound is not soluble (solubility of less than 0.1 g/l, or even 0.01 g/l, at 25° C.) and which is capable of inducing the precipitation of the intermediate compound when the nonsolvent is introduced into the reaction medium.

An aqueous solution, such as water, is an example of a nonsolvent of the intermediate compound Ya.

The solvent of step a) comprises dimethylacetamide, the process may comprise, between steps a) and b), the addition of a solvent of the intermediate compound Ya to the reaction medium obtained at the end of step a), in order to fluidize it. Specifically, the following step b), which is carried out in the presence of a chlorinating agent, often leads to the formation of Vilsmeier complexes between the chlorinating agent and dimethylacetamide, which may thicken the reaction medium by crystallizing. This solvent of the intermediate compound Ya is typically one of the solvents described below (preferably those free of an amide function) for steps a), b), c) and/or d), and is preferably propylene carbonate.

The process may comprise, at the end of step b):
the addition of a nonsolvent of the intermediate compound Yb into the reaction medium obtained at the end of step b), whereby the intermediate compound Yb precipitates from the reaction medium and a reaction medium comprising a liquid phase and a precipitate is obtained,
the separation of the precipitate and the liquid phase, for example by filtration, settling or centrifuging, then
the dissolving of the precipitate in a solvent of the intermediate compound Yb in order to obtain a solution which is used to carry out step c).

The nonsolvent of the intermediate compound Yb is generally an aqueous solution, preferably an aqueous solution of an alkali-metal ion acetate, such as sodium acetate. The solvent of the intermediate compound Yb is typically one of the solvents described below for steps a), b), c) and/or d).

The process is preferably free of purification of the intermediate compound Yb. Typically, when the three steps of addition of a nonsolvent/separation of the precipitate/dissolving of the precipitate are carried out, the precipitate is not subjected to any purification between the separation of the precipitate and the liquid phase and the dissolving thereof in a solvent of the intermediate compound Yb, and in particular no recrystallization. The process according to the invention can be applied on an industrial scale and makes it possible in particular to obtain cumulative yields of at least 80% for the one-pot sequence of steps a), b), c) and d).

The preparation process as according to the invention also has the advantage of generating soluble intermediates (the term "soluble" means that the process does not generate crystals).

Definitions

The process according to the invention comprises a sequence, preferably a one-pot sequence:
of steps a) and b), in which the intermediate compound Ya resulting from the acylation (step a)) is not isolated before carrying out the chlorination (step b)), and/or
steps b) and c), in which the intermediate compound Yb resulting from the chlorination (step b)) is not purified before carrying out the amidation (step c)) and/or
steps c) and d) in which the intermediate compound Yc resulting from the amidation (step c)) is not isolated before carrying out the deprotection (step d)).

In one embodiment, in the process,
the intermediate compound Ya resulting from the acylation (step a)) is not isolated before carrying out the chlorination (step b)), the intermediate compound Yb resulting from the chlorination (step b)) is not purified before carrying out the amidation (step c)), and the intermediate compound Yc resulting from the amidation (step c)) is not isolated before carrying out the deprotection (step d)).

In one embodiment, in the process, the intermediate compound Ya resulting from the acylation (step a)) is not separated from the reaction medium obtained at the end of step a) before carrying out the chlorination (step b)), the intermediate compound Yb is not separated from the intermediate compound Ya optionally present in the reaction medium at the end of step b) before carrying out the amidation step (step c)), and the intermediate compound Yc resulting from the amidation (step c)) is not separated from the reaction medium obtained at the end of step c) before carrying out the deprotection (step d)).

A one-pot preparation process or reaction sequence is a process/sequence in which a synthesis intermediate, for example AATI, undergoes several successive and/or simultaneous reactions in its reaction medium, avoiding the steps of separation and purification of the intermediate compounds (process free of separation and purification of the intermediate compounds Ya and/or Yc, and preferably free of purification of the intermediate compound Yb).

The term "organo-iodinated" compound means an organic compound comprising at least one carbon atom and at least one iodine atom, for example 1, 2, 3, 4 or 5 iodine atoms, preferably 3. Said organic compound optionally comprises one or more atoms of hydrogen, oxygen, nitrogen, sulfur, phosphorus, halogen or a combination of these atoms. Preferably, the organo-iodinated compound comprises one or more atoms of hydrogen (hydrocarbon-based compound), oxygen, nitrogen and optionally chlorine.

The term "acylation" means a chemical reaction during which an acyl group is added to an organic compound such as AATI by the action of an acylating agent.

The term "chlorination", also known as chloride formation, means the substitution of an atom and/or a group of atoms of an organic compound with a chlorine atom, preferably the substitution of a hydroxyl group (—OH) with a chlorine atom (—Cl), by the action of a chlorinating agent or chlorinator, more preferably the double substitution of the hydroxyl groups (—OH) present on two carboxylic acid functions with a chlorine atom (—Cl).

The term "amidation" means the combination of an amine with a chemical group of a compound.

The term "deprotection" means the removal, typically with a deprotecting agent, of a functional group introduced into the molecule from a chemical function in order to mask all or part of its reactivity.

According to the present invention, the expression "reaction medium" denotes the medium in which the steps a) of acylation, b) of chlorination, c) of amidation and d) of deprotection take place. According to one embodiment, said reaction medium comprises at least one solvent and at least one reagent such as AATI and/or an acylating agent and/or a chlorinating agent and/or an amine and/or a deprotecting agent.

The term "isolation" denotes:

the separation of an intermediate compound Ya, Yb and/or Yc from the other organo-iodinated compound(s) optionally present in the reaction medium, or even the separation of an intermediate compound Ya, Yb and/or Yc from the reaction medium.

optionally followed by its (their) purification(s) Methods for separation and/or purifying an organo-iodinated compound are known to those skilled in the art. Filtration, chromatography (on grafted or ungrafted silica, for example), centrifuging, solvent extraction, crystallization, adsorption (for example onto charcoal) and distillation may be cited by way of example. Preferably, the process is free of a step of separating the intermediate compound Ya from the reaction medium obtained at the end of step a) and/or of a step of separating the intermediate compound Yc from the reaction medium obtained at the end of step c). The process is generally free of filtration of the compound Ya between steps a) and b) (no separation of the compound Ya) and/or it is generally free of filtration of the compound Yc between steps c) and d) (no separation of the compound Yc). Given hereinbelow are examples of no separation of an intermediate compound Ya, Yb and/or Yc from the other organo-iodinated compound(s):

at the end of step a), the intermediate compound Ya is not separated from the AATI optionally present in the reaction medium at the end of step a), and/or at the end of step b), the intermediate compound Yb is not separated from the intermediate compound Ya optionally present in the reaction medium at the end of step b), and/or at the end of step c), the intermediate compound Yc is not separated from the intermediate compound Yb optionally present in the reaction medium at the end of step c).

Process for the Preparation of an Organo-Iodinated Compound

According to one embodiment, the steps a) of acylation, b) of chlorination, c) of amidation and d) of deprotection of the process according to the invention are carried out without isolation of at least one intermediate compound chosen from Ya and Yc in a single reactor or in several reactors, preferably in a single reactor.

According to one embodiment, step a) of acylation of 2,4,6-triiodo-5-aminoisophthalic acid of formula (A) below:

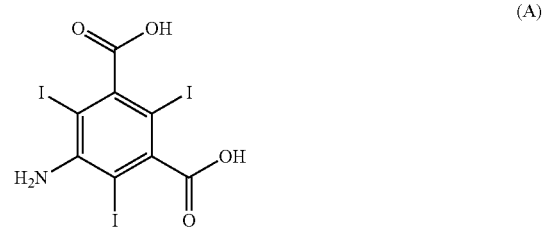 [SMILES: Nc1c(I)c(C(=O)O)c(I)c(C(=O)O)c1I]

(A)

is carried out by an acyl chloride, preferably by chloroacetyl chloride (CAC) or acetoxyacetyl chloride (AAC), more preferably by acetoxyacetyl chloride.

AAC has the advantage of not being considered to be a toxic and carcinogenic, mutagenic and reprotoxic (CMR) compound and it acts very rapidly as an acylating agent.

According to one particular embodiment, the process according to the invention comprises the following steps:

a) acylation of 2,4,6-triiodo-5-aminoisophthalic acid of formula (A) below:

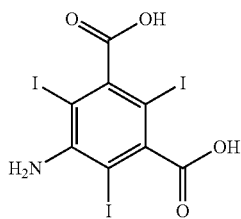

(A)

by a compound of general formula (I) below:

$$R_2-C(O)Cl \quad (I),$$

$R_2$ being a $-CH_2-GP$ group wherein GP is a leaving group chosen from a halide, an acetate, a mesylate, a tosylate and a triflate, $R_2$ being preferably chosen from $-CH_2Cl$ and

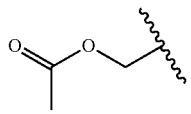 [SMILES: *COC(C)=O]

in order to obtain an intermediate compound Ya; then
b) chlorination of the intermediate compound Ya in order to obtain an organo-iodinated intermediate compound Yb of general formula (II) below:

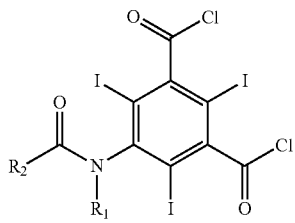

(II)

$R_1$ being H or a methyl group, preferably H, and
$R_2$ being as defined above, then
c) amidation of the organo-iodinated intermediate compound Yb in order to obtain an intermediate compound Yc; then
d) deprotection of the intermediate compound Yc,
the steps a), b), c) and d) being carried out without isolation of at least one intermediate compound chosen from Ya and Yc, preferably without isolation of the intermediate compounds Ya and Yc.

Step c) is generally carried out in the presence of an amine of formula (IV):

$$R_3-NH_2 \quad (IV),$$

in which $R_3$ represents an alkyl group comprising 1 to 6 carbon atoms, notably 2, 3 or 4 carbon atoms, said alkyl group optionally being substituted by one or more hydroxyl groups, preferably two hydroxyl groups, or a salt thereof. The preferred amine is aminopropanediol.

Preferably, the amount of amine of formula (IV) used during step c) is such that the molar ratio of the amine of formula (IV) relative to the AATI used during step a) is from 1.5 to 4.0, notably from 1.8 to 3.0, and preferably from 2.0 to 2.3.

The organo-iodinated compound Yd obtained at the end of step d), preferably the compound of general formula (V) as defined below, is of use as a synthesis intermediate of the ioversol contrast agent.

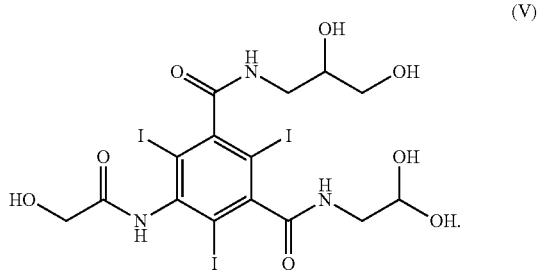

(V)

Ioversol is sold under the brand name Optiject® or Optiray® and has the following chemical formula:

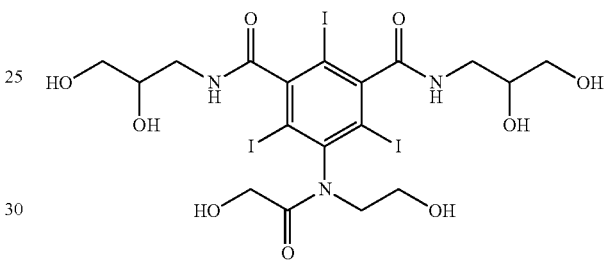

According to one embodiment, steps a), b), c) and/or d) are carried out in the presence of an aprotic polar solvent.

According to one embodiment, steps a), b), c) and/or d) are carried out in the presence of at least one solvent chosen from the group consisting of dimethylacetamide, propylene carbonate, acetonitrile and tetrahydrofuran or a mixture thereof. Preferably, the solvent comprises a mixture of dimethylacetamide and propylene carbonate. In particular, for the reasons described in detail above, it is advantageous for the solvent of step b) to be a mixture of propylene carbonate and dimethylacetamide.

In one preferred embodiment:
the solvent of step a) is dimethylacetamide, and/or
the solvent of step b) is a mixture of propylene carbonate and dimethylacetamide, and/or
the solvent of step c) and/or of step d) is a mixture of dimethylacetamide and an aqueous solution.

Since steps a), b), c) and/or d) are preferably carried out in a one-pot manner, step b) is carried out in the reaction medium resulting from step a), step c) is carried out in the reaction medium resulting from step b) and step d) is carried out in the reaction medium resulting from step c): the solvent(s) used and also the amount(s) thereof are therefore preferably identical. According to one embodiment, during step b) one or more solvent(s) may be added to the one(s) used for step a) and/or during step c) one or more solvent(s) may be added to the one(s) used for step b) and/or during step d) one or more solvent(s) may be added to the one(s) used for step c).

According to another embodiment, the ratio, in liters per kilogram, between the amount of solvent (in liters) and the amount of 2,4,6-triiodo-5-aminoisophthalic acid (in kg) is between 5:1 and 1:1, preferably 3:1 or 2.5:1. Such ratios advantageously make it possible to dissolve all of the intermediate compound Yb, which makes it possible to optimize the subsequent steps c) and d).

Generally, the organo-iodinated compound obtained at the end of step d) has the formula (VI) below:

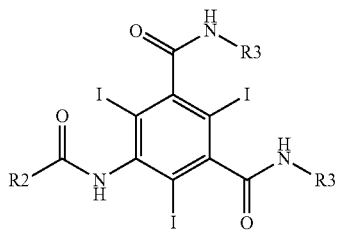

in which $R_2$ and $R_3$ are as defined above.

Steps a), b), c) and d) may optionally be followed by a step e) of alkylating the compound obtained at the end of step d) with an alkylating agent, notably ethylene oxide or an alkylating agent of formula (VII):

$R_4\text{-GP'}$ (VII)

in which:
  $R_4$ represents an alkyl group comprising from 1 to 6 carbon atoms, notably 2, 3 or 4 carbon atoms, said alkyl group optionally being substituted by one or more hydroxyl groups, and
  GP' is a leaving group, notably chosen from a halide, a mesylate, a tosylate and a triflate.

The alkylating agent is typically 2-chloroethanol or ethylene oxide, and step e) leads to the formation of ioversol.

The embodiments described below for each of steps a) to d) may be combined together.

Acylation Step a)

According to one embodiment, the acylation of step a) is carried out in the presence of an acylating agent chosen from chloroacetyl chloride and acetoxyacetyl chloride.

These acylating agents have the following chemical formulae:

| Name of acylating agent | CAS number | Chemical formula |
|---|---|---|
| Chloroacetyl chloride | 79-04-09 |  |
| Acetoxyacetyl chloride | 13831-31-7 | |

According to one embodiment, the acylation of step a) is carried out in the presence of an acylating agent, preferably an acyl chloride, present in an amount between 1 and 1.5 molar equivalents with respect to the amount of 2,4,6-triiodo-5-aminoisophthalic acid; preferably between 1.1 and 1.3, for example 1.1 or 1.3 molar equivalents with respect to the amount of 2,4,6-triiodo-5-aminoisophthalic acid.

Chlorination Step b)

According to one embodiment, the chlorination of step b) is carried out in the presence of a chlorinating agent chosen from the group consisting of thionyl chloride, phosphorus oxychloride, phosphorus trichloride, oxalyl chloride, phosphorus pentachloride, methanoyl dichloride and a mixture thereof. According to one embodiment, the chlorination of step b) is carried out in the presence of a reagent chosen from the group consisting of thionyl chloride, phosphorus trichloride, phosphorus pentachloride and a mixture thereof. Preferably, the chlorinating agent is thionyl chloride, since the phosphorus derivatives mentioned above generate phosphate salts which are more polluting and the removal of which complicates the process.

According to one particular embodiment, the amount of chlorinating agent is between 2 and 6 molar equivalents with respect to the amount of 2,4,6-triiodo-5-aminoisophthalic acid, preferably between 2.5 and 5 equivalents, more preferably between 3 and 5 equivalents, for example 3.5 or 5 equivalents, more preferably still between 3.2 and 4 equivalents with respect to the amount of 2,4,6-triiodo-5-aminoisophthalic acid.

According to one embodiment, step a) is carried out for a period of 2 to 70 hours, preferably 2 to 24 h; and/or step b) is carried out for a period of 2 to 22 hours, preferably 4 to 12 h.

Step a) is typically carried out at a temperature of from 10° C. to 70° C., preferably from 15° C. to 60° C., more preferably still from 30° C. to 60° C., notably from 45° C. to 55° C., for example at 50° C. When the temperature is too low, this reduces the yield of step a) and therefore of the process, and when it is too high, more impurities are generated, thus the purity is reduced. The temperature ranges above are optimal for reducing the appearance of certain impurities while maintaining an economically acceptable reaction time.

Step b) is preferably carried out at a temperature of from −15° C. to 30° C., preferably from −10° C. to 10° C., more preferably still from 0° C. to 10° C.

Amidation Step c)

According to one embodiment, the amidation of step c) is carried out in the presence of aminopropanediol (also known as APD).

Preferably, the amidation of step c) is carried out in the presence of a base, notably an inorganic base, for example sodium hydroxide (NaOH). Inorganic bases are generally less toxic than certain organic bases such as triethylamine. Moreover, using an organic base comprising an amine function necessitates adding a step of removing the ammonium salt formed from this organic base, which makes the process more complex and makes it difficult to implement the process without isolating the intermediate compound Yc. The use of an inorganic base such as NaOH generates salts, such as NaCl, which are less soluble in the reaction medium obtained at the end of step b) and therefore which will be more easily removable from the reaction medium.

Step c) is generally carried out in the presence of an aqueous solution, typically an aqueous solution of an inorganic base, such as an aqueous solution of NaOH. There was a technical prejudice to carrying out step c) in the presence of an aqueous solution, since those skilled in the art would have expected the degradation of the acyl chloride functions of the intermediate compound Yb in the presence of such a solution, which degradation would result in reforming the intermediate compound Ya. Water is known to be detrimental to amidation starting from an acyl chloride.

Step c) is generally carried out at a temperature of from 5° C. to 30° C., preferably from 5° C. to 20° C., more preferably still from 5° C. to 15° C. Such temperatures make it possible in particular to reduce the content of polar impurities (for example monoamidated impurities).

Deprotection Step d)

Those skilled in the art are capable of determining, in view of their general knowledge illustrated by the work "Greene's Protective Groups in Organic Synthesis" by Wiley (ISBN-13: 978-0471697541) how to deprotect as a function of the nature of the protective group and therefore of the acylating group used in step a).

According to one embodiment, the deprotection of step d) is carried out firstly by the addition of a base then by the addition of an acid. Preferably, use will be made of a base chosen from organic bases or inorganic bases. More preferably, use will be made of an organic base chosen from a mixture of triethylamine and methanol, a mixture of pyridine and water and mixtures thereof. More preferably, use will be made of an inorganic base chosen from sodium hydroxide, aqueous ammonia, a mixture of aqueous ammonia and toluene, potassium carbonate ($K_2CO_3$), a mixture of hydrazine and methanol and mixtures thereof. Preferably, use will be made of an inorganic acid. More preferably, use will be made of an inorganic acid chosen from hydrochloric acid, phosphoric acid, sulfuric acid and mixtures thereof.

According to one embodiment, the deprotection of step d) is carried out firstly by addition of a base then by addition of an acid followed by addition of a solvent. The solvent is preferably chosen from isopropanol, ethanol, methanol and mixtures thereof, more preferably isopropanol, ethanol and mixtures thereof.

According to one embodiment, the deprotection of step d) is carried out firstly by addition of a base such as an inorganic base, typically a mixture of sodium hydroxide and water, then by addition of an acid such as an inorganic acid, for instance hydrochloric acid, optionally followed by the addition of isopropanol. This embodiment is particularly suitable when the acylating agent of step a) is acetoxyacetyl chloride. Thus, the acetyl group on the compound obtained in step c) is deprotected. Preferably, the deprotection of step d) is carried out at a temperature of from 15° C. to 70° C., preferably from 20° C. to 60° C., more preferably still from 30° C. to 55° C.

When chloroacetyl chloride is used as acylating agent in step a), the deprotection of step d) is carried out by

- addition of an acid aqueous solution, such as an aqueous solution of hydrochloric acid, typically to a pH of from 3.0 to 4.5, pressurized at a pressure of from 1.05 to 1.5 bar, for example 1.2 bar, and heating to a temperature of between 110° C. and 130° C., and pH of the reaction medium between 3.0 and 4.5 by addition of a base, for example sodium hydroxide, then
- addition of a base, for example an aqueous solution of NaOH, until the pH of the reaction medium reaches 4.5 to 5.5.

The examples that appear below are presented by way of illustration and have no limiting effect on the invention.

EXAMPLES

The term "V" is understood to denote a volume ratio, namely the volume of a reagent or of a solvent relative to 1 kg of AATI.

The term "eq." is understood to denote a molar equivalent number, namely the ratio between the number of moles of a reagent and the number of moles of AATI.

Example 1: Synthesis According to the Invention of an Ioversol Synthesis Intermediate Synthesis Scheme
MP602 Starting from AATI

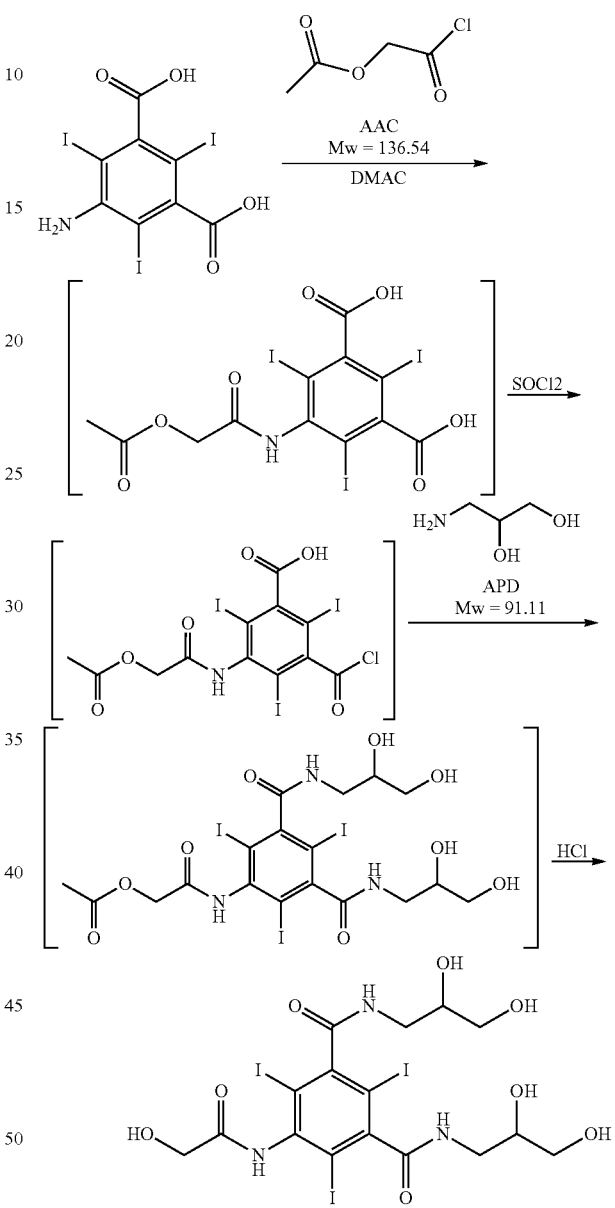

Acylation Step:

2-chloro-2-oxoethyl acetate (also known as AAC) (281 g, 1.15 eq.) is dissolved in dimethylacetamide (DMAC) (1.35 l) and AATI (1 kg, 1.0 eq.) is gradually added at 50° C. The reaction medium is mixed for 6 hours at 50° C. Propylene carbonate (1.15 l) is added and the reaction is cooled to 5° C.

Chlorination Step:

Thionyl chloride $SOCl_2$ (745 g, 3.5 eq.) is added at 5° C. over 2 hours and the reaction medium is mixed for 5 hours at 5° C.

The reaction medium is added to an aqueous solution of sodium acetate (AcONa) so as to precipitate the "DiCOAlike" synthesis intermediate. The suspension is filtered and the solid portion is redissolved in DMAC (1.5 ml) to obtain a solution.

Amidation Step:

A mixture of aminopropanediol (APD) (359 g, 2.2 eq.) and an aqueous 30% sodium hydroxide (NaOH) solution (359 ml) is added to the solution over 6 hours. The reaction medium is mixed for 2 hours at 12.5° C.

Deprotection Step:

Water (1 l) and an aqueous 30% sodium hydroxide (NaOH) solution (359 ml) are added at 50° C. over 2 hours and 30 minutes. 37% hydrochloric acid (HCl) (900 ml) is then added at 50° C. and the reaction is cooled to 5° C. The suspension is filtered, washed with an isopropanol (IPA)/water mixture and dried. The yield obtained is 83% and the purity obtained is 99%.

Example 2: Synthesis of Ioversol from the Synthesis Intermediate Obtained According to the Invention The compound obtained in example 1 is then alkylated using 2-chloroethanol or ethylene oxide. The compound thus obtained is then purified and dried in order to obtain ioversol.

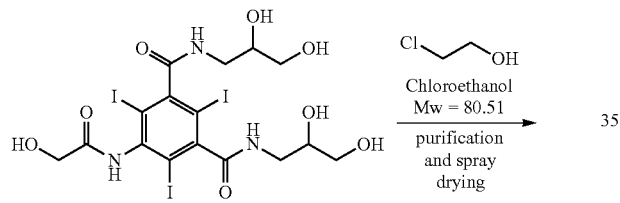

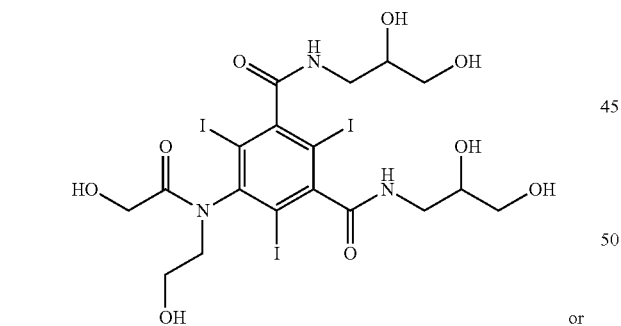

or

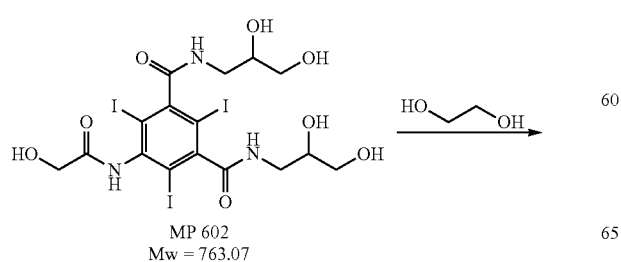

MP 602
Mw = 763.07

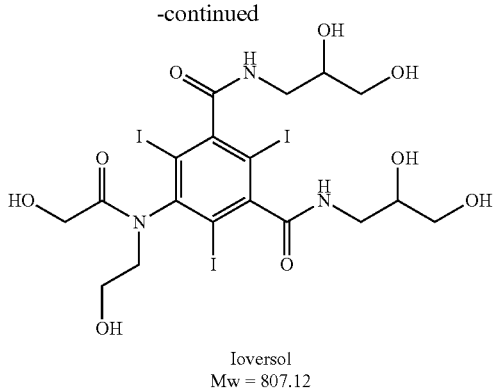

Ioversol
Mw = 807.12

The invention claimed is:

1. A process for preparing an organo-iodinated compound, comprising the following steps:

a) acylating 2,4,6-triiodo-5-aminoisophthalic acid of formula (A) below:

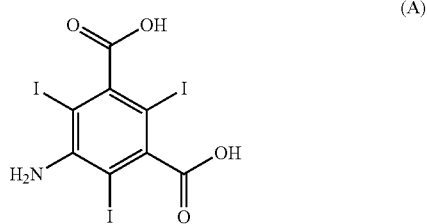 [SMILES: Nc1c(I)c(C(=O)O)c(I)c(C(=O)O)c1I]

with a compound of formula (I) below:

$$R_2—C(O)Cl \qquad (I),$$

wherein R2 is a -CH$_2$-GP group and GP is a leaving group selected from the group consisting of a halide, an acetate, a mesylate, a tosylate, and a triflate to obtain an intermediate compound Ya of formula (Ya) below:

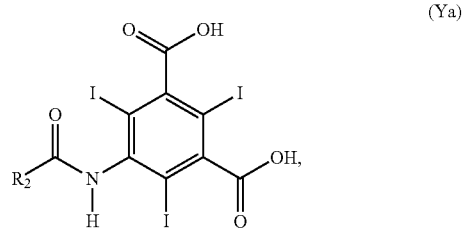

wherein the compound of formula (I) is present in an amount between 1 and 1.5 molar equivalents with respect to the amount of the 2,4,6-triiodo-5-aminoisophthalic acid;

b) chlorinating the intermediate compound Ya to obtain an organo-iodinated intermediate compound Yb of formula (II) below:

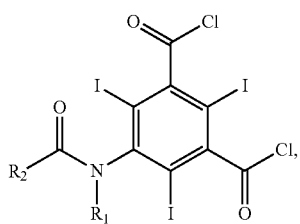

(II)

wherein $R_1$ is H;

c) amidating the organo-iodinated intermediate compound Yb in the presence of an inorganic base and of an amine of formula (IV) below:

$R_3$—$NH_2$ (IV), wherein R3 represents an alkyl group comprising 1 to 6 carbon atoms, said alkyl group optionally being substituted by one or more hydroxyl groups, or a salt thereof to obtain an intermediate compound Yc of formula (Yc) below:

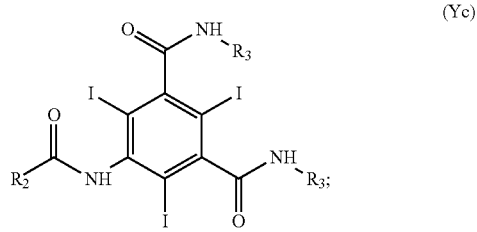

(Yc)

and d) deprotecting the intermediate compound Yc to obtain to organo-iodated compound Yd of formula (Yd) below:

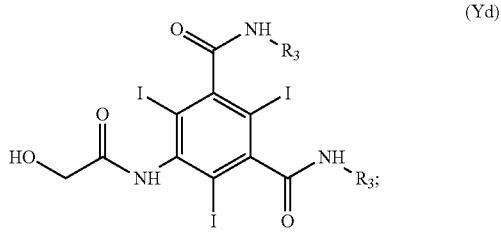

(Yd)

the steps a), b), c) and d) being carried out without isolation of at least one intermediate compound chosen from Ya and Yc.

2. The preparation process of claim 1, free of a step of separating the intermediate compound Ya from the reaction medium obtained at the end of step a).

3. The preparation process of claim 1, free of a step of separating the intermediate compound Yc from the reaction medium obtained at the end of step c).

4. The preparation process of claim 1, wherein R2 is —$CH_2Cl$ or

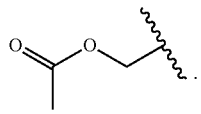 [SMILES: *COC(C)=O]

5. The preparation process of claim 1, wherein the steps a), b), c) and d) are carried out without isolation of the intermediate compounds Ya and Yc.

6. The preparation process of claim 1, wherein the steps a), b), c) and d) are carried out without purification of the intermediate compound Yb.

7. The preparation process of claim 1, free of addition of a nonsolvent of the intermediate compound Ya during step a) and between steps a) and b).

8. The preparation process of claim 1, wherein the steps a), b), c) and d) are carried out in a single reactor.

9. The preparation process of claim 1, wherein the steps a), b), c) and d) are carried out in the presence of a solvent selected from the group consisting of dimethylacetamide, propylene carbonate, acetonitrile, tetrahydrofuran, and mixtures thereof.

10. The preparation process of claim 1, wherein step b) is carried out in a solvent that is a mixture of propylene carbonate and dimethylacetamide.

11. The preparation process of claim 1, wherein step c) is carried out in the presence of an aqueous solution.

12. The preparation process of claim 9, wherein:
the solvent of step a) is dimethylacetamide; and/or
the solvent of step c) and/or of step d) is a mixture of dimethylacetamide and an aqueous solution.

13. The preparation process of claim 1, wherein the chlorination of step b) is carried out in the presence of a chlorinating agent selected from the group consisting of thionyl chloride, phosphorus oxychloride, phosphorus trichloride, oxalyl chloride, phosphorus pentachloride, methanoyl dichloride, and mixtures thereof.

14. The preparation process of claim 1 further comprising:
adding a nonsolvent of the intermediate compound Yb into the reaction medium obtained at the end of step b), whereby the intermediate compound Yb precipitates from the reaction medium and a reaction medium comprising a liquid phase and a precipitate is obtained;
separating the precipitate and the liquid phase; and
dissolving of the separated precipitate in a solvent of the intermediate compound Yb to obtain a solution used to carry out step c).

15. The preparation process as claimed in claim 1, wherein the amidation of step c) is carried out with 3-amino-1,2-propanediol.

16. The preparation process as claimed in claim 1, wherein the deprotection of step d) is carried out with sodium hydroxide, hydrochloric acid, or a mixture thereof.

* * * * *

UNITED STATES PATENT AND TRADEMARK OFFICE
CERTIFICATE OF CORRECTION

| | | |
|---|---|---|
| PATENT NO. | : 11,472,767 B2 | Page 1 of 1 |
| APPLICATION NO. | : 17/265107 | |
| DATED | : October 18, 2022 | |
| INVENTOR(S) | : Stéphan Pellinghelli and Myriam Petta | |

It is certified that error appears in the above-identified patent and that said Letters Patent is hereby corrected as shown below:

On the Title Page

Item (12), should read: Pellinghelli et al.

Item (72), The name of the first named inventor is listed backwards. It should be listed as Stéphan Pellinghelli.

Signed and Sealed this
Twenty-second Day of October, 2024

*Katherine Kelly Vidal*

Katherine Kelly Vidal
*Director of the United States Patent and Trademark Office*